United States Patent [19] [11] Patent Number: 4,824,663
Wirth et al. [45] Date of Patent: Apr. 25, 1989

[54] BIOCIDAL MACROEMULSIONS CONTAINING POLYVINYL ALCOHOL

[75] Inventors: Wolfgang Wirth, Hennef; Heinz J. Niessen, Bergisch-Gladbach; John W. S. Goossens; Hans Schulze, both of Cologne, all of Fed. Rep. of Germany

[73] Assignee: Bayer Aktiengesellschaft, Leverkusen, Fed. Rep. of Germany

[21] Appl. No.: 837,465

[22] Filed: Mar. 7, 1986

[30] Foreign Application Priority Data

Mar. 12, 1985 [DE] Fed. Rep. of Germany ....... 3508642
Apr. 11, 1985 [DE] Fed. Rep. of Germany ....... 3512916

[51] Int. Cl.$^4$ ................. A01N 25/04; A01N 57/00; A01N 57/14
[52] U.S. Cl. .......................... 424/78; 514/72; 514/73; 514/938; 252/312; 424/406
[58] Field of Search ............. 252/312; 424/DIG. 8, 424/406, 78; 514/72, 73

[56] References Cited

U.S. PATENT DOCUMENTS

| 3,839,554 | 10/1974 | Corkins | 424/78 |
| 4,071,617 | 1/1978 | Graves et al. | 424/78 |
| 4,145,439 | 3/1979 | Schulze et al. | 514/471 |
| 4,299,841 | 11/1981 | Geering | 424/DIG. 8 |
| 4,303,640 | 12/1981 | Fuyama et al. | 424/78 |
| 4,304,587 | 12/1981 | Cummings | 514/147 |
| 4,500,348 | 2/1985 | Hausmann et al. | 71/103 |
| 4,656,163 | 4/1987 | Anderson et al. | 514/128 |
| 4,725,589 | 2/1988 | Tsuboi et al. | 514/128 |

FOREIGN PATENT DOCUMENTS

| 1209361 | 8/1986 | Canada . |
| 1209362 | 8/1986 | Canada . |
| 0083437 | 7/1983 | European Pat. Off. . |
| 0111580 | 6/1984 | European Pat. Off. . |
| 2805251 | 8/1978 | Fed. Rep. of Germany . |
| 2936265 | 3/1980 | Fed. Rep. of Germany . |
| 2452249 | 10/1980 | France . |

OTHER PUBLICATIONS

Federal Register, vol. 49, No. 235 (Dec. 5, 1984), p. 47493.

Primary Examiner—John F. Terapane
Assistant Examiner—Gary Geist
Attorney, Agent, or Firm—Sprung Horn Kramer & Woods

[57] ABSTRACT

The present invention relates to new macroemulsions which contain
0.001 to 60 percent by weight of at least one active compound from the class comprising the phosphates and/or carbamates,
0 to 50 percent by weight of aromatic diluents,
0.001 to 20 percent by weight of polyvinyl alcohol having a mean molecular weight of between 5,000 and 150,000 and a content of acetate groups of between 2 and 30 mol %, and/or
0.001 to 20 percent by weight of a nonlphenol/propylene oxide/ethylene oxide adduct of the formula

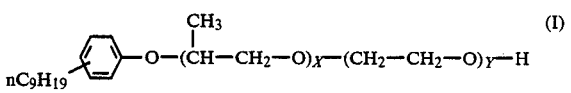

in which
X represents integers from 10 to 50 and
Y represents integers from 15 to 65,
and/or
0.001 to 20 percent by weight of ethylene oxide/propylene oxide/ethylene oxide block copolymers having a mean molecular weight of between 2,000 and 8,000 and HLB values of between 8 and 30,
and water and, if appropriate, additives, and
in which the oil phase is dispersed in the aqueous phase in the form of droplets having a mean particle diameter of 0.1 to 3.0 μm.

9 Claims, No Drawings

BIOCIDAL MACROEMULSIONS CONTAINING POLYVINYL ALCOHOL

The present invention relates to new macroemulsions which contain active compounds from the class comprising the phosphates and/or carbamates, a process for the preparation of the macroemulsions, and their use for combating pests.

A large number of aqueous emulsions of agrochemically active compounds have already been disclosed. Preparations of this type can be produced, for example, by dissolving the generally water-insoluble active compounds in an amount of organic solvent, and adding an amount of emulsifier, such that sufficiently stable emulsions are formed when these formulations are diluted with water to the concentrations for use. However, the solvents present frequently result in the concentrates possessing disadvantages because of flammability, toxicological properties, toleration by plants, and odor.

In the case of agrochemically active compounds which are not hydrolyzed by water when a certain pH value is established, or which by their very nature are insensitive to hydrolysis, the organic solvents or mixtures of organic solvents can be completely or at least partially replaced with water in the preparation of the formulations of plant protection agents. When suitable emulsifiers are added, microemulsions are obtained, that is to say oil-in-water emulsions in which the oil phase is dispersed in the aqueous phase in the form of droplets having a diameter of less than 0.1 $\mu$m (see EP-OS (European Published Specification) No. 0,062,181, EP-OS (European Published Specification) No. 0,107,009 and EP-OS (European Published Specification) No. 0,107,023). The disadvantage of these microemulsions is that the active compounds present are generally released very rapidly, with the result that the toxicity of the preparations, instead of being more advantageous, is frequently even less favorable than in the case of the concentrates in which larger amounts of organic solvents are present. Furthermore, microemulsion concentrates of this type are often stable to phase separation only within a narrow temperature range.

Macroemulsions of agrochemically active compounds are also known, that is to say oil-in-water emulsions, in which the oil phase is dispersed in the aqueous phase in the form of droplets having a mean diameter of 0.5 $\mu$m or greater. In the known macroemulsions, added thickeners are present in order to effect stabilization (see U.S. Pat. No. 4,303,640). Owing to the thickeners present, however, the viscosity of these macroemulsions is so high that volumetric metering of the preparations is made difficult, and substantial residual amounts of plant protection agents remain in the emptied containers.

Finally, oil-in-water emulsions of certain agrochemically active compounds, which contain polyvinyl alcohol as stabiliser, in addition to conventional emulsifiers, are also known (see EP-OS (European Published Specification) No. 0,111,580). However, the toxicological properties of such emulsions, whose mean droplet size is <1 $\mu$m, are less advantageous than those of the corresponding emulsions in which only polyvinyl alcohol is present as a stabilizer. In particular, an undesired irritating effect on skin and mucous membranes occurs in some cases during application of the spray liquors diluted to the concentration for use.

The present invention relates to new macroemulsions relates to
0.001 to 60 percent by weight of at least one active compound from the class comprising the phosphates and/or carbamates,
0 to 50 percent by weight of aromatic diluents,
0.001 to 20 percent by weight of polyvinyl alcohol having a mean molecular weight of between 5,000 and 150,000 and a content of acetate groups of between 2 and 30 mol %, and/or
0.001 to 20 percent by weight of a nonylphenol/propylene oxide/ethylene oxide adduct of the formula

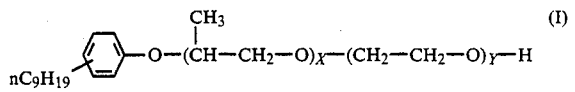

in which
X represents integers from 10 to 50 and
Y represents integers from 15 to 65,
and/or
0.001 to 20 percent by weight of ethylene oxide/propylene oxide/ethylene oxide block copolymers having a mean molecular weight of between 2,000 and 8,000 and HLB values of between 8 and 30,
and water and, if appropriate, additives, and
in which the oil phase is dispersed in the aqueous phase in the form of droplets having a mean particle diameter of 0.1 to 3.0 $\mu$m.

Furthermore, it has been found that the macroemulsions according to the invention can be prepared by a process in which
an aqueous solution which contains between 1 and 25 percent by weight of polyvinyl alcohol having a mean molecular weight of between 5,000 and 150,000 and a content of acetate groups of between 2 and 30 mol %, and/or
an aqueous solution which contains between 1 and 30 percent by weight of a nonylphenol/propylene oxide/ethylene oxide adduct of the formula

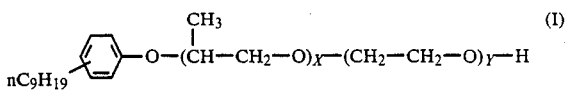

in which
X represents integers from 10 to 50 and
Y represents integers from 15 to 65,
and/or
an aqueous solution which contains between 1 and 30 percent by weight of ethylene oxide/propylene oxide/ethylene oxide block copolymers having a mean molecular weight of between 2,000 and 8,000 and HLB values of between 8 and 30
are added to
at least one active compound from the class comprising the phosphates and/or carbamates, if appropriate in the presence of an aromatic diluent at temperatures between 10° C. and 30° C., while stirring,
the resulting emulsion, if appropriate after additives have been introduced beforehand, is then homogenized at temperatures between 10° C. and 70° C. using a suitable apparatus, and
if appropriate, additives are then introduced and the emulsion is made up with water to the desired concentration.

Finally, it has been found that the macroemulsions according to the invention are very suitable for combating pests.

It must be regarded as extremely surprising that the macroemulsions according to the invention have a less irritating effect on the skin and mucous membranes than the corresponding previously known emulsions which contain organic solvents and conventional emulsifiers. The fact that the formulations according to the invention are stable, over a relatively wide temperature range, in regard to degradation of the active compound, crystallization of the active compound and separation is also unexpected.

The macroemulsions according to the invention are also distinguished by a number of advantages. Thus, they can be prepared in a simple manner using readily available auxiliaries. The addition of thickeners and emulsifiers is unnecessary. Furthermore, the macroemulsions according to the invention have a low viscosity so that volumetric metering can be carried out without difficulties. The advantageous toxicological properties, the good dispersibility in water and the good physical stability of the emulsions according to the invention at both low and high temperatures should also be singled out.

One or more insecticidal, acaricidal and/or nematicidal substances from the class comprising the phosphates and/or carbamates are present as active components in the macroemulsions according to the invention. Suitable active compounds are both those substances which are liquid at room temperature and those which are solid at room temperature. The following may be mentioned as individual examples of active compounds of this type:

O-ethyl-O-(3-methyl-4-methylthio-phenyl) isopropylamidophosphate

O-ethyl-S,S-di-phenyl dithiophosphate

O,O-dimethyl-O-(4-methylthio-3-methylphenyl) thionophosphate

O-ethyl-S-propyl O-(2,4-dichloro-phenyl) thionophosphate

O,O-diethyl-O-(4-nitro-phenyl) thionophosphate

O,O-dimethyl-O-(4-nitro-phenyl) thionophosphate

O-ethyl-O-(4-methylthio-phenyl)-S-propyl dithiophosphate (O,O-diethyl-thionophosphoryl)-α-oximino-phenylacetonitrile O,O-diethyl-O-(3-chloro-4-methyl-7-coumarinyl) thiophosphate S-[1,2-bis-(ethoxycarbonyl)-ethyl]-O,O-dimethyl dithiophosphate O-ethyl-O-(2-isopropoxycarbonyl-phenyl)-N-isopropylthionophosphoramide 2-isopropoxy-phenyl N-methylcarbamate 2-ethylthiomethyl-phenyl N-methyl-carbamate 2,3-dihydro-2,2-dimethyl-7-benzofuranyl methyl-carbamate 3,5-dimethyl-(4-methylthio-phenyl) N-methylcarbamate.

All customary aromatic solvents or solvents or solvent mixtures which boil between 100° C. and 290° C. may be present in the macroemulsions according to the invention. Toluene, ethylbenzene, chlorobenzene, xylenes, alkylated benzenes having on average 9 carbon atoms, such as the types of solvent known under the name Solvesso$^R$, and naphthalene which is optionally substituted by alkyl having 1 to 3 carbon atoms are preferred.

The macroemulsions according to the invention contain either polyvinyl alcohol of the abovementioned type or nonyl phenol/propylene oxide/ethylene oxide adducts of the formula (I) or ethylene oxide/propylene oxide/ethylene oxide block copolymers of the abovementioned type or mixtures of one or more of the abovementioned components.

Preferred polyvinyl alcohols are those which have a mean molecular weight of between 20,000 and 125,000 and a content of acetate groups of 2 to 30 mol %.

The following may be mentioned as examples of polyvinyl alcohols of this type: polyvinyl alcohol having a mean molecular weight of 47,000 and a content of acetate groups of 12 mol %, polyvinyl alcohol having a mean molecular weight of 99,000 and a content of acetate groups of 12 mol %, polyvinyl alcohol having a mean molecular weight of 81,000 and a content of acetate groups of 12 mol %, polyvinyl alcohol having a mean molecular weight of 25,000 and a content of acetate groups of 12 mol %, polyvinyl alcohol having a mean molecular weight of 82,000 and a content of acetate groups of 17 mol%, polyvinyl alcohol having a mean molecular weight of 85,000 and a content of acetate groups of 23 mol%, polyvinyl alcohol having a mean molecular weight of 27,000 and a content of acetate groups of 29 mol% and polyvinyl alcohol having a mean molecular weight of 75,000 and a content of acetate groups of 4mol%.

In each case, the content of acetate groups is a measure of the degree of hydrolysis of the polyvinyl alcohol prepared from polyvinyl acetate.

Preferred nonyl phenol/propylene oxide/ethylene oxide adducts are those compounds of the formula (I) in which X represents integers from 20 to 45 and Y represents integers of from 20 to 60.

Preferred ethylene oxide/propylene oxide/ethylene oxide block copolymers are compounds of this type which have a mean molecular weight of between 2,500 and 7,000 and HLB values (=hydrophilic-lipophilic balance) of between 9 and 27. The HLB value is a measure of the hydrophilicity or lipophilicity of the substance used.

Suitable additives, which may be present in the macroemulsions according to the invention, are dyestuffs, preservatives, antifoams, antifreezes, crystallization inhibitors, odor improvers and acids.

In this connection, anthraquinone dyestuffs, azo dyestuffs and phthalocyanine dyestuffs may be mentioned as examples of dyestuffs.

2-Hydroxybiphenyl, sorbic acid, p-hydroxybenzaldehyde, methyl p-hydroxybenzoate, benzaldehyde, benzoic acid, propyl p-hydroxybenzoate, p-nitrophenol and the preservative on the market under the name Preventol ® and Dimamin ® may be mentioned as examples of preservatives.

Suitable antifoams are silicone oils.

Glycol, glycerol, urea, sugar and polyethylene glycol may be mentioned as examples of antifreezes.

Examples of crystallization inhibitors are alkylphenols which are condensed with 1 to 8 moles of ethylene oxide per mole. In this connection, nonylphenol which is condensed with 2 moles of ethylene oxide per mole may be mentioned specifically.

Perfume oils can be employed as odor improvers.

Examples of acids which may be present as additives in the macroemulsions according to the invention are inorganic and organic acids, such as phosphoric acid, citric acid and benzoic acid.

The macroemulsions according to the invention contain water as the continuous phase. In the case of concentrates, the amount of water is relatively small. In the case of highly dilute emulsions, substantial amounts of water are present.

In the macroemulsions according to the invention, the oil phase (=disperse phase) is dispersed in the form of droplets in the aqueous phase. The size of the oil droplets can be varied within a certain range. In general, the mean particle diameter is between 0.1 and 3.0 μm, preferably between 0.2 and 2.5 μm.

In the macroemulsions according to the invention, the percentages of the components present can be varied within relatively wide ranges. The amount of active compounds from the class comprising the phosphates and carbamates is in general between 0.001 and 60 percent by weight, preferably between 0.01 and 50 percent by weight. The amount of aromatic diluent is in general between 0 and 50 percent by weight, preferably between 0 and 40 percent by weight. Where polyvinyl alcohol is present, the amount of this component is in general between 0.001 and 20 percent by weight, preferably between 0.01 and 15 percent by weight. If a nonylphenol/propylene oxide/ethylene oxide adduct of the formula (I) is present, the amount of this component is in general between 0.001 and 20 percent by weight, preferably between 0.01 and 10 percent by weight. Where an ethylene oxide/propylene oxide/ethylene oxide block copolymer is present, the amount of this component is in general between 0.001 and 20 percent by weight, preferably between 0.01 and 10 percent by weight. Additives may be present in amounts of between 0.1 and 20 percent by weight, preferably between 0.2 and 15 percent by weight.

The percentage of water in the macroemulsions according to the invention is in each case the difference between 100 percent by weight and the sum of the percentages of the remaining components.

In the preparation of the macroemulsions according to the invention, it is preferable to use all those components which have already been mentioned in connection with the description of the macroemulsions according to the invention as being preferred or by way of example.

If an active compound which is in the liquid state at room temperature is used in the process according to the invention, this active compound is generally employed as such. However, it is also possible to use a solution of the particular active compound in an aromatic diluent.

If an active compound which is in the solid state at room temperature is used in the process according to the invention, a solution of the particular substance in an aromatic diluent is employed.

If the process according to the invention is carried out using polyvinyl alcohol, this component is employed in the form of aqueous solutions. The concentrations of these solutions can be varied within a certain range. In general, aqueous solutions which contain between 1 and 25 percent by weight, preferably between 2 and 20 percent by weight, of polyvinyl alcohol are used.

If the process according to the invention is carried out using a nonylphenol/propylene oxide/ethylene oxide adduct of the formula (I), this component is used in the form of aqueous solutions. The concentrations of these solutions can be varied within a certain range. In general, aqueous solutions which contain between 1 and 30 percent by weight, preferably between 5 and 25 percent by weight, of a nonylphenol/propylene oxide/ethylene oxide adduct of the formula (I) are used.

If the process according to the invention is carried out using an ethylene oxide/propylene oxide/ethylene oxide block copolymer, this component is used in the form of aqueous solutions. The concentrations of these solutions can be varied within a certain range. In general, aqueous solutions which contain between 1 and 30 percent by weight, preferably between 5 and 25 percent by weight, of block copolymers are used.

In the first stage of the process according to the invention, a pre-emulsion is prepared, and this is then homogenized in the second stage of the process.

Both in the first stage and in the second stage of the process according to the invention, the reaction temperatures can be varied within a certain range. The first stage is carried out in general at temperatures between 10° C. and 30° C., preferably between 15° C. and 25° C. The second stage is carried out in general at temperatures between 10° C. and 70° C., preferably between 15° C. and 65° C.

Homogenization in the second stage of the process according to the invention is preferably effected using high-pressure homogenizers or jet dispersers in which the pressure drop per dispersing nozzle is between 10 and 50 bar. Jet dispersers of this type are already known (see EP-OS (European Published Specification) No. 0,101,007).

In carrying out the process according to the invention, the procedure adopted is in general as follows:

in the first stage, either one or more liquid active compounds or a solution of solid and/or liquid active compounds in an aromatic diluent are initially introduced, and an aqueous polyvinyl alcohol solution and/or an aqueous soluton of a nonylphenol/propylene oxide/ethylene oxide adduct of the formula (I) and/or an aqueous solution of an ethylene oxide/propylene oxide/ethylene oxide block copolymer and, if appropriate, additives are added at temperatures between 10° C. and 30° C., while stirring, then, in a second stage, the resulting pre-emulsion is homogenized at temperatures between 10° C. and 70° C. with the aid of a suitable apparatus and if appropriate, additives are then introduced and the emulsion is made up with water to the desired concentration.

The amounts of the components are chosen so that macroemulsions are formed in which the concentrations of the individual constituents are in the abovementioned ranges.

The macroemulsions according to the invention possess very good insecticidal, acaricidal and/or nematicidal properties. They can therefore be employed for combating the appropriate animal pests, such as insects, arachnida and/or nematodes, in agriculture, in horticulture, in the household and hygiene sectors and in the veterinary sector.

The macroemulsions according to the invention can be applied either in the prepared form or after prior dilution. The amount used depends on the concentration of the active compounds in the formulation and on the particular indication.

The macroemulsions according to the invention are applied, if appropriate after prior dilution, by the customary methods, that is to say, for example, by spraying, atomizing or watering.

The examples which follow illustrate the preparation of the macroemulsions according to the invention.

Preparation examples

EXAMPLE 1

A solution of 6 parts by weight of an ethylene oxide/propylene oxide/ethylene oxide block copolymer, having a mean molecular weight of 6,500 and an HLB value of 15.0, in 59 parts by weight of demineralized water is added to 25 parts by weight of O,O-dimethyl-O-(3-methyl-4-methylthio-phenyl) thiophosphate at room temperature, while stirring gently. The resulting pre-eulsion is homogenized at 20° C. using a jet disperser in which the pressure drop per dispersing nozzle is 40 bar. Thereafter, 10 parts by weight of glycerol are added, and stirring is continued for a further 5 minutes. A macroemulsion in which the oil phase is dispersed in the aqueous phase in the form of droplets having a mean particle diameter of 1 μm is obtained in this manner.

The macroemulsion obtained remained stable even after storage for eight weeks in a thermal cycling chamber at temperatures between −15° C. and +30° C., and at +50° C.

EXAMPLE 2

A solution of 6 parts by weight of an ethylene oxide/propylene oxide/ethylene oxide block copolymer, having a mean molecular weight of 3,000 and an HLB value of 15.0, in 49 parts by weight of demineralized water is added, at room temperature, to a gently stirred solution of 25 parts by weight of O-ethyl-O-(3-methyl-4-methylthiophenyl) isopropylamido-phosphate in 20 parts by weight of an aromatic solvent known under the name Solvesso 100$^R$. The resulting pre-emulsion is heated to 50° C. and homogenized using a jet disperser in which the pressure drop per dispersing nozzle is 40 bar. Thereafter, 10 parts by weight of glycerol are added and stirring is continued for a further 5 minutes. A macroemulsion in which the oil phase is dispersed in the aqueous phase in the form of droplets having a mean diameter of 1 μm is obtained in this manner.

The macroemulsion thus obtained remained stable even after storage for eight weeks in a thermal cycling chamber at temperatures between −15° C. and +30° C., and at +50° C.

EXAMPLE 3

A solution of 2.4 parts by weight of a nonylphenol/propylene oxide/ethylene oxide adduct having the approximate formula $$nC_9H_{19}\text{-}\phi\text{-}O\text{-}(CH(CH_3)\text{-}CH_2\text{-}O)_{24}\text{-}(CH_2\text{-}CH_2\text{-}O)_{40}\text{-}H$$

in 45.6 parts by weight of demineralized water is added to 25 parts by weight of O-ethyl-O-(2,4-dichlorophenyl) S-n-propyl dithiophosphate at room temperature, while stirring gently. The resulting pre-emulsion is heated to 50° C. and homogenized using a jet disperser in which the pressure drop per dispersing nozzle is 40 bar. Thereafter, 10 parts by weight of glycerol and 19.4 parts by weight of dimeralized water are added and stirring is continued for a further 5 minutes. A macroemulsion in which the oil phase is dispersed in the aqueous phase in the form of droplets having a mean particle diameter of 1 μm is obtained in this manner.

The macroemulsion obtained remained stable even after storage for eight weeks in a thermal cycling chamber at temperatures between −15° C. and +30° C., and at +50° C.

It will be understood that the specification and examples are illustrative but not limitative of the present invention and that other embodiments within the spirit and scope of the invention will suggest themselves to those skilled in the art.

What is claimed is:

1. A macroemulsion consisting essentially of
    0.001 to 60 percent by eight of at least one active compound from the group consisting of the insecticidal, acaricidal and/or nematicidal phosphates and carbamates,
    0 to 50 percent by weight of an aromatic diluent,
    0.001 to 20 percent by weight of polyvinyl alcohol having a mean molecular weight of between 5,000 and 150,000 and a content of acetate groups of between 2 and 30 mol % and/or
    0.001 to 20 percent by weight of a nonylphenol/propylene oxide/ethylene oxide adduct of the formula $$nC_9H_{19}\text{-}\phi\text{-}O\text{-}(CH(CH_3)\text{-}CH_2\text{-}O)_X\text{-}(CH_2\text{-}CH_2\text{-}O)_Y\text{-}H \quad (I)$$

in which
      X represents integers from 10 to 50 and
      Y represents integers from 15 to 65,
      and/or
    0.001 to 20 percent by weight of an ethylene oxide/propylene oxide/ethylene oxide block copolymer having a mean moleculr weight of between 2,000 and 8,000 and HLB values of between 8 and 30,
    and water
    and wherein
      the oil phase of said macroemulsion is dispersed in the aqueous phase of said macroemulsion in the form of droplets having a mean particle diameter of 0.1 to 3.0 μm.

2. A macroemulsion according to claim 1, wherein said phosphate is O,O-dimethyl-O-(3-methyl-4-methylthiophenyl) thiophosphate.

3. A macroemulsion according to claim 1, wherein said phosphate comprises O-ethyl-O-(3-methyl-4-methylthio-phenyl) isopropyl-amido-phosphate.

4. A macroemulsion according to claim 1, wherein said phosphate comprises O-ethyl-O-(2,4-dichlorophenyl) S-n-propyl dithio-phosphate.

5. A macroemulsion according to claim 1, wherein said aromatic diluent is selected from the group consisting of toluene, ethylbenzene, chlorobenzene, xylenes, alkylated benzenes having on average 9 carbon atoms and naphthalene which is optionally substituted by alkyl having 1 to 3 carbon atoms.

6. A macroemulsion according to claim 1, consisting essentially of
    0.01 to 15 percent by weight of polyvinyl alcohol having a mean molecular weight of between 20,000 and 125,000 and a content of acetate groups of 2 to 30 mol % and/or
    0.01 to 10 percent by weight of a nonylphenol/propylene oxide/ethylene oxide block copolymer having a mean molecular weight of between 2,500 and 7,000 and HLB values of between 9 and 27.

7. A macroemulsion according to claim 1, wherein said additives comprise dyestuffs, preservatives, antifoams, antifreezes, crystallization inhibitors, odor improvers and acids.

8. A macroemulsion according to claim 1, wherein said oil phase is dispersed in said aqueous phase in the form of droplets having a mean particle diameter of between 0.2 μm and 2.5 μm.

9. A method of combating pests comprising applying to said pests or habitat thereof the macroemulsion of claim 1.

* * * * *

UNITED STATES PATENT AND TRADEMARK OFFICE
CERTIFICATE OF CORRECTION

PATENT NO. : 4,824,663

DATED : April 25, 1989

INVENTOR(S) : Wirth et al

It is certified that error appears in the above-identified patent and that said Letters Patent is hereby corrected as shown below:

| | |
|---|---|
| Col. 8, line 16 | Delete "/or" |
| Col. 8, line 50 | Delete "comprises" and substitute --is-- |
| Col. 8, line 53 | Delete "comprises" and substitute --is-- |
| Col. 9, line 3 & 4 | Delete "wherein said" and substitute --containing-- |
| Col. 9, line 4 | Delete "comprise" and substitute --selected from the group consisting of-- |

Signed and Sealed this

Twelfth Day of June, 1990

Attest:

HARRY F. MANBECK, JR.

*Attesting Officer*      *Commissioner of Patents and Trademarks*